(12) United States Patent
Ourian

(10) Patent No.: US 11,439,462 B2
(45) Date of Patent: Sep. 13, 2022

(54) SYSTEM AND METHOD FOR LASER SKIN RESURFACING

(71) Applicant: Simon Ourian, Beverly Hills, CA (US)

(72) Inventor: Simon Ourian, Beverly Hills, CA (US)

(*) Notice: Subject to any disclaimer, the term of this patent is extended or adjusted under 35 U.S.C. 154(b) by 61 days.

(21) Appl. No.: 16/653,640

(22) Filed: Oct. 15, 2019

(65) Prior Publication Data

US 2020/0113630 A1    Apr. 16, 2020

Related U.S. Application Data

(60) Provisional application No. 62/746,085, filed on Oct. 16, 2018.

(51) Int. Cl.
*A61B 18/20* (2006.01)
*A61B 18/00* (2006.01)

(52) U.S. Cl.
CPC .. *A61B 18/203* (2013.01); *A61B 2018/00017* (2013.01); *A61B 2018/00029* (2013.01); *A61B 2018/0047* (2013.01); *A61B 2018/00577* (2013.01)

(58) Field of Classification Search
CPC ........ A61B 18/203; A61B 2018/00017; A61B 2018/00029; A61B 2018/0047; A61B 2018/00577; A61B 18/20–18/28; A61N 5/06–2005/073
See application file for complete search history.

(56) References Cited

U.S. PATENT DOCUMENTS

| 6,077,294 A | 6/2000 | Cho et al. |
| 6,149,644 A | 11/2000 | Xie |
| 6,165,170 A | 12/2000 | Wynne et al. |
| 8,182,473 B2 | 5/2012 | Altshuler et al. |
| 9,962,225 B2 * | 5/2018 | McMillan ............ A61B 18/20 |

(Continued)

OTHER PUBLICATIONS

Zimmer, Cryo 6 Cold Air Chiller Device—Cryo Therapy by Zimmer; https://zimmerusa.com/products/cryo-therapy/cryo-6/ (Year: 2022).*

(Continued)

*Primary Examiner* — Jonathan T Kuo
(74) *Attorney, Agent, or Firm* — Omni Legal Group; Omid E Khalifeh; Lara A. Petersen

(57) ABSTRACT

A system and method for laser skin resurfacing is provided. The system comprises a topical numbing composition, cryogenically cooled air, a fractional laser, and one or more topical compositions. The topical numbing composition and the cryogenically cooled air are operative to reduce patient pain and discomfort. The cryogenically cooled air is further operative to protect the patient's skin from thermal damage. The fractional laser is operative to ablate the patient's skin cells. The method comprises the steps of applying a topical numbing composition to an area of a patient's skin comprising the treatment area; directing cryogenically cooled air and a fractional laser to the treatment area; and applying one or more topical compositions to the treatment area. The system and method stimulates collagen production in the patient's skin, diminishes inflammation and damage to the patient's skin, reduces patient recovery time following a laser resurfacing procedure, and ultimately, maximizes patient satisfaction with the procedure.

13 Claims, 1 Drawing Sheet

(56) References Cited

U.S. PATENT DOCUMENTS

| | | | | |
|---|---|---|---|---|
| 10,004,734 B2* | 6/2018 | Scherer | ............... | A61K 9/06 |
| 2006/0004306 A1* | 1/2006 | Altshuler | ............ | A61H 39/002 |
| | | | | 601/3 |
| 2006/0211665 A1* | 9/2006 | Ranawat | ............ | A61K 31/485 |
| | | | | 514/171 |
| 2009/0069741 A1* | 3/2009 | Altshuler | ............ | A61B 5/441 |
| | | | | 604/22 |
| 2010/0247693 A1* | 9/2010 | Marini | ............ | A61K 38/08 |
| | | | | 424/769 |
| 2013/0197473 A1* | 8/2013 | McMillan | ............ | A61N 5/062 |
| | | | | 604/501 |
| 2016/0095592 A1* | 4/2016 | Levinson | ............ | A61F 15/005 |
| | | | | 606/219 |
| 2017/0209439 A1* | 7/2017 | Scherer | ............ | A61K 45/06 |

OTHER PUBLICATIONS

Mayo Clinic, Vitamin A, https://www.mayoclinic.org/drugs-supplements-vitamin-a/art-20365945; Nov. 13, 2020 (Year: 2020).*

Niederreither, K., Dollé, P. Retinoic acid in development: towards an integrated view. Nat Rev Genet 9, 541-553 (2008). https://doi.org/10.1038/nrg2340 (Year: 2008).*

* cited by examiner

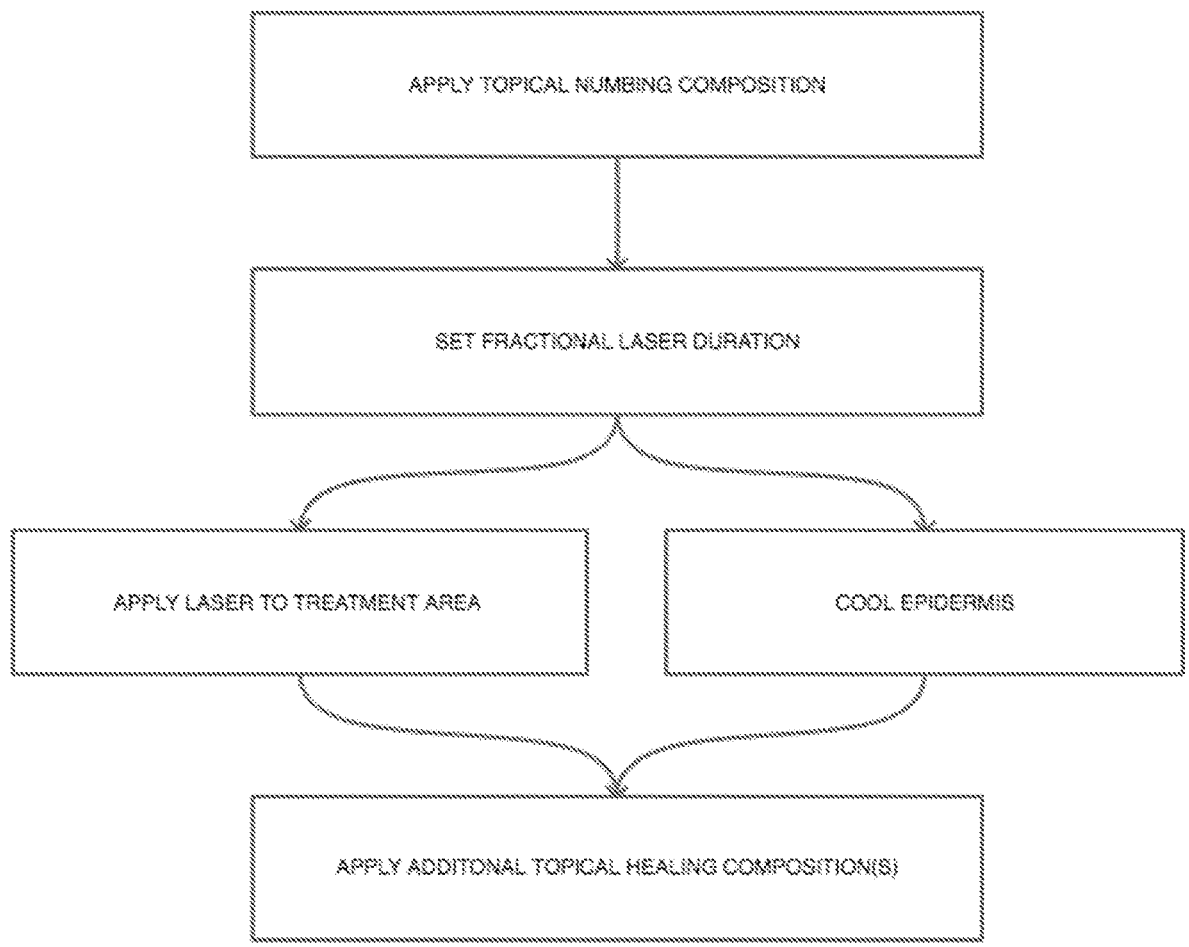

SYSTEM AND METHOD FOR LASER SKIN RESURFACING

CROSS-REFERENCE TO RELATED APPLICATIONS

Pursuant to 35 U.S.C. § 120, this patent application relies on the benefit of U.S. Patent App. No. 62/746,085 filed on Oct. 16, 2018. The content of said application is incorporated herein by reference in its entirety.

GOVERNMENT CONTRACT

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to dermatological treatments and, more particularly, to a method of skin resurfacing using fractional lasers in combination and in sequence with topical compositions.

BACKGROUND

It is only natural that over time, elasticity and structural integrity of human skin diminishes as the body's inclination to produce the collagen protein that is responsible for supporting the functional integrity of mammalian tissue decreases. Indeed, for millennia, humans have attempted to modify their appearance, and particularly signs of aging through various means in response to this natural process. Various methods of using tape to stretch wrinkled skin, surgically manipulating sagging folds, and even painful procedures involving delivering needles into the skin at intervals have been offered as methods for regaining a youthful appearance.

In the last few decades, less invasive laser procedures have become popular for their ability to selectively damage portions of skin and stimulate collagen production, which can have revitalizing effects. Thus far, however, certain disadvantages have plagued laser skin resurfacing procedures. For instance, the procedures can be painful as skin cells are effectively radiated to death. Indeed, depending on the type and duration of the laser resurfacing procedure, recovery times can be inconveniently long. Sometimes, the treated area of skin can be particularly unsightly, burned, and even peeling during recovery. As such, there is a need for improved methods and systems in the field of laser skin resurfacing.

SUMMARY

The present disclosure is directed to improved laser skin resurfacing methods and systems. More particularly, such methods comprise, in sequence, applying a topical numbing composition to an area of a patient's skin comprising the treatment area, directing fractional lasers to the treatment area along with cryogenically cooled air, and then applying one or more additional topical compositions to the skin, such additional compositions formulated to reduce pain and inflammation and, in some embodiments, stimulate collagen production. Using the methods described, it is contemplated that a dermatologist and/or other medical practitioner may treat various skin conditions such as wrinkles, melasma, stretchmarks, discoloration, and scarring, among others, in a manner that corrects the condition and, in some cases, even slows the apparent aging process.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

One or more of the above-disclosed embodiments, in addition to certain alternatives, are provided in further detail below with reference to the attached FIGURES. The disclosed subject matter is not, however, limited to any particular embodiment disclosed.

One or more of the above-disclosed embodiments, in addition to certain alternatives, are provided in further detail below with reference to the attached FIGURES. The disclosed subject matter is not, however, limited to any particular embodiment disclosed.

Objects and Advantages

Some objects and advantages of the system and method for laser skin resurfacing are:

Stimulating the production of collagen.

Treating one or more undesirable skin conditions.

Reducing a patient's recovery time following laser skin resurfacing procedures.

Reducing risks of post inflammatory pigmentation following laser resurfacing procedures.

Reducing patient discomfort associated with ablative laser resurfacing procedures.

Maximizing patient satisfaction as a result of reducing discomfort during laser skin resurfacing procedures.

Additional objects and advantages will become evident from the description of the invention.

BRIEF DESCRIPTION OF THE DRAWINGS

FIG. 1 shows a flow chart illustrating the method for laser skin resurfacing in accordance with some embodiments of the invention.

The disclosed embodiments may be better understood by referring to the FIGURES in the attached drawings, as provided below. The attached FIGURES are provided as non-limiting examples for providing an enabling description of the method and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

In some embodiments, a method for laser skin resurfacing comprises applying topical numbing compositions to skin to be treated—or the treatment area, delivering laser beams according to certain specifications to such treatment area, applying cryo-chilled air to the treatment area, and applying additional topical compositions to the treatment area in a prescribed manner following the laser treatment.

More particularly, a topical numbing composition may be an analgesic cream, gel, or liquid such as lidocaine, epinephrine, or a combination of the same. It is contemplated that applying a topical numbing composition to the treatment area prior to bombarding it with lasers will reduce a patient's discomfort over the course of treatment with the laser. This may also beneficially avoid a need of treating a patient with stronger anesthetics which, while frequently effective to completely eliminate sensations, are also known to involve some undesirable side effects and risk factors.

After applying the topical numbing composition, a practitioner, such as a dermatologist, physician, physician's assistant or another person qualified to operate a laser device for the stated purpose, may apply sequential bursts of laser beams to the treatment area. The treatment area may be, for example only and not limitation, skin covering a person's face, neck, décolletage, hands, feet, buttocks, or any other area of skin having laser-treatable conditions. These conditions may include, as non-limiting examples, wrinkles, stretchmarks (or striae), acne, acne scars, melasma, liver spots, other discoloration, and many other conditions.

In some embodiments, the laser is a fractional, or fractionated, laser such as a carbon dioxide ($CO_2$) laser, operative to ablate portions of the mid-layer of skin, and more particularly, the dermal collagen, by delivering microscopic beams of light to the treatment area. While the laser beams will of course, desirably, ablate the skin cells which they contact, it is contemplated that providing a fractioned laser beam will ensure that healthy skin remains interspersed among such ablated portions. Thus, ablated portions are relatively small and far apart from one another. Since the ablated skin is interspersed with healthy skin, the patient's body responds to repair relatively smaller portions of the skin than it otherwise would, this may result in a relatively shorter recovery period. Indeed, the patient's risk of experiencing scarring and post inflammatory pigmentation may also be reduced. While fractionating the laser beam in this manner may reduce recovery time as well as risks of undesirable side effects, additional steps comprise the method in furtherance of the advantages and objects of the invention.

In some embodiments, the fractionated laser may be applied to the treatment area in a series of adjacent squares. The size of each square may approximately correspond to the cross-sectional laser output. In some embodiments, the square may be about 20 mm by about 20 mm. The number of beams that the laser is fractionated into may vary. In some embodiments, the laser may be fractionated into about 100 to about 400 beams per square. In some embodiments, the fractionated laser may be split into about 225 beams per square. In some embodiments, the number of beams may depend on the desired beam density. For instance, setting the laser to a beam density of 1.4 mm may ensure that 1.4 mm of healthy skin remains between each ablated portion of skin. The optimal beam density may vary depending on the condition being treated and the patient's possible risk factors, therefore the cited density is presented by way of example only and not limitation.

In some embodiments, the laser may operate at energy about 22 to about 24 mJ, or more particularly about 23.4 mJ.

Over the course of operation, the laser may pulse on and off for a desirable duration in order to avoid subjecting targeted tissues from experiencing too much laser contact. This is because prolonged exposure could irreversibly damage the skin. The duration of each laser pulse may be selected based on factors such as the Fitzpatrick skin type, which is based on melanin pigment in the skin and is known to those skilled in the art. For example, patients having Fitzpatrick skin types I, II, or III—pale, fair or dark white skin tones—may be subject to pulses duration of about 0.6 to about 9.0 ms, or from about 1.0 to about 8.0 ms. Patients having Fitzpatrick skin type IV, or light brown skin, may instead be subject to pulses in the range of about 0.5 ms to about 4.0 ms. Patients having Fitzpatrick skin type V or VI—or brown to dark brown or black skin may benefit from pulses in the range of about 0.2 to about 0.5 ms. This is because darker skin may be prone to develop post inflammatory pigmentation after ablation. Thus, decreasing the blast time for darker skin may avoid such side effects.

In some embodiments, the time taken to repeat each pulse may vary as well. In some embodiments, the laser may pulse once—for the set duration—about every 0.5 seconds. In some embodiments, such as embodiments requiring more precision, this time may be increased. In other embodiments, the time to repeat each pulse may be decreased.

Once treatment over a line adjacent squares defining the width of the treatment area is performed, the provider of such treatment may move downward to treat another row, contiguous to the first, of the treatment area and continue with the same method, applying the laser in a series of parallel lines, until the full treatment area has been pulsed with the laser beam. Overlapping treatment areas may be avoided in order to prevent excessive damage to the patient's skin, however, whether overlapping occurs over the course of treatment should not be seen to limit the invention. Indeed, in some cases it may be desirable to overlap treatment rows and/or columns. For instance, slightly overlapping each row and column by, for example, about one millimeter or more, may blend the treated areas and avoid leaving behind unsightly stripes of untreated skin. This may be particularly undesirable as a sign that a person has undergone a cosmetic procedure, which is sometimes the subject of some social stigma.

Cold air may also be applied to the skin directly before and after application of the laser. This air may protect the epidermis from thermal damage over the course of skin resurfacing treatments and further reduce pain and swelling and even reduce recovery period by one or more days. Indeed, the entire surface of the skin may be cooled using a device operative to concentrate cryogenically chilled air to desirable regions. For example, in some embodiments, the air may be blasted from a machine such as the Cryo Cold Air Chiller Device manufactured by Zimmer® at a temperature of about −6 degrees Celsius.

More particularly, a hose emitting the cold air may be applied simultaneously with the laser or separately. When apply simultaneously, the hose may be held together with a handle portion of the laser handle. Although other methods of reducing swelling and pain are available, it is contemplated that using cold air device may be beneficial over other methods, including cryogen spray, and even ice packs because the cooling air can be applied to the skin before, during, and after the laser energy treatment without physically interfering with the laser beam.

Following laser treatment, one or more additional topical compositions may be applied to the treated area. For instance, one such additional topical composition may be a creamy ointment comprising one or more of the following active ingredients: betamethasone, lidocaine, and epinephrine. In some embodiments, such additional topical composition may comprise about 0.1% betamethasone by volume, 0.5% lidocaine by volume, and 1:10000 epinephrine by volume of the composition. Instructions may be given to the patient to self-apply the healing ointment at regular or otherwise prescribed intervals over the course of about 12 to about 72 hours post-treatment, or in some embodiments about 24 to about 48 hours post treatment. In some embodiments, application of such ointment may be supervised by the provider to ensure compliance and/or effective use.

Still another additional topical composition may be provided with instructions for use to simulate collagen production following laser treatment. In an embodiment, the additional topical composition may comprise any or a combination of 8% hydroquinone by weight of the composition, 0.1% retinoic acid by weight of the composition, 0.4% hydrocortisone by weight of the composition, 1% clindamycin by weight of the composition, and 3% kojic acid by weight of the composition.

Yet still another of the additional topical compositions may comprise 4% kojic acid by weight of the composition, and 0.1% retinoic acid by weight of the composition. In some embodiments, the patient may be instructed to apply one or more of these additional compositions to the treated area at regular, or even prescribed, intervals for at least 2 to about 12 months following treatment. One example of a regular or prescribed interval may be daily. Another example of a regular or prescribed interval may be twice daily, once in the morning and once at night. Of course, such intervals are provided as clarifying examples only and do not limit the invention.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. Accordingly, it is intended that the invention not be limited, except as by the appended claims.

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the system and method for laser skin resurfacing with which that terminology is associated. In general, the terms used in the following claims should not be constructed to limit the system and method for laser skin resurfacing to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the system and method for laser skin resurfacing is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the system and method for laser skin resurfacing.

What is claimed is:

1. A system for laser skin resurfacing, comprising:
    a topical numbing composition operative to reduce a patient's discomfort comprising lidocaine and epinephrine;
    air cryogenically cooled to about −6° C. operative to protect the patient's skin from thermal damage and reduce pain and inflammation;
    a fractional laser, operative to ablate one or more cells of the patient's skin; and
    one or more topical compositions comprising kojic acid, hydroquinone, hydrocortisone, clindamycin, and retinoic acid.

2. The system of claim 1, wherein the topical numbing composition is a combination of lidocaine and epinephrine.

3. The system of claim 1, wherein the fractional laser is a carbon dioxide laser.

4. The system of claim 1, further comprising
    up to 0.5% wt. lidocaine; and
    up to 0.01% wt. epinephrine.

5. The system of claim 1, further comprising
    up to 4.0% wt. kojic acid; and
    up to 0.1% wt. retinoic acid.

6. The system of claim 1, wherein one of the one or more topical compositions comprises hydroquinone, hydrocortisone, and clindamycin; and another one of the one or more topical compositions comprises retinoic acid and kojic acid.

7. The system of claim 6, wherein the one or more topical compositions comprise
up to 8.0% wt. hydroquinone;
up to 0.1% wt. retinoic acid;
up to 0.4% wt. hydrocortisone;
up to 1.0% wt. clindamycin; and
up to 3.0% wt. kojic acid.

8. The system of claim 6, wherein the one or more topical compositions stimulate collagen production in the patient's skin.

9. A method for laser skin resurfacing, comprising:
applying a topical numbing composition comprising betamethasone, lidocaine, and epinephrine to an area of a patient's skin comprising the treatment area, wherein the treatment area comprises one or more skin conditions;
directing air cryogenically cooled to about −6° C., and a fractional laser to the treatment area; and
after directing the laser to the treatment area, applying one or more topical compositions comprising at least kojic acid and retinoic acid to the treatment area.

10. The method of claim 9, wherein the one or more skin conditions are wrinkles, melasma, acne, stretchmarks, discoloration, or scarring.

11. The method of claim 9, wherein the fractional laser, the cryogenically cooled air, and the one or more topical compositions treat the one or more skin conditions.

12. The method of claim 9, wherein the one or more topical compositions are formulated to reduce pain and inflammation.

13. The method of claim 9, wherein the one or more topical compositions are formulated to stimulate collagen production.

* * * * *